United States Patent [19]

Kaltenbach et al.

[11] Patent Number: 5,500,071
[45] Date of Patent: Mar. 19, 1996

[54] MINIATURIZED PLANAR COLUMNS IN NOVEL SUPPORT MEDIA FOR LIQUID PHASE ANALYSIS

[75] Inventors: Patrick Kaltenbach, Bischweier, Germany; Laurie Mittelstadt, Belmont; Sally Swedberg, Los Altos, both of Calif.

[73] Assignee: Hewlett-Packard Company, Palo Alto, Calif.

[21] Appl. No.: 326,111

[22] Filed: Oct. 19, 1994

[51] Int. Cl.$^6$ .................................................. B32B 31/28
[52] U.S. Cl. ..................... 156/272.8; 156/273.3; 156/292; 156/257; 210/198.2; 210/656; 422/70; 73/61.52
[58] Field of Search ............. 204/180.1; 156/272.8, 156/273.3, 272.2, 379.6, 217, 290, 292, 252, 257, 258; 210/198.2, 656; 422/70; 73/61.52; 95/85; 96/101, 105, 107

[56] References Cited

U.S. PATENT DOCUMENTS

| | | | |
|---|---|---|---|
| 3,770,529 | 11/1973 | Anderson | 156/272.8 X |
| 3,919,768 | 11/1975 | Pittman et al. | 156/217 X |
| 3,953,056 | 4/1976 | Roberts | 156/257 X |
| 4,392,907 | 7/1983 | Shirato et al. | 156/257 X |
| 4,713,963 | 12/1987 | Sharp . | |
| 4,865,729 | 9/1989 | Saxena et al. | 210/198.2 |
| 4,908,112 | 3/1990 | Pace . | |
| 5,132,012 | 7/1992 | Miura et al. | 210/198.2 |

FOREIGN PATENT DOCUMENTS

| | | | |
|---|---|---|---|
| 0230056 | 11/1985 | Japan . | |
| 0230058 | 11/1985 | Japan | 210/198.2 |
| 0191962 | 8/1986 | Japan | 422/70 |
| 2087858 | 4/1987 | Japan | 422/70 |
| 2310467 | 12/1990 | Japan | 210/198.2 |

*Primary Examiner*—David A. Simmons
*Assistant Examiner*—Steven J. Helmer

[57] ABSTRACT

Miniaturized planar column devices are described for use in liquid phase analysis, the devices comprising microstructures fabricated by laser ablation in a variety of novel support substrates. Devices formed according to the invention include associated laser-ablated features required for function, such as analyte detection means and fluid communication means. Miniaturized columns constructed under the invention find use in any analysis system performed on either small and/or macromolecular solutes in the liquid phase and may employ chromatographic and/or electrophoretic separation means.

6 Claims, 7 Drawing Sheets

MINIATURIZED PLANAR COLUMNS IN NOVEL SUPPORT MEDIA FOR LIQUID PHASE ANALYSIS

TECHNICAL FIELD

The present invention relates generally to miniaturized planar column technology for liquid phase analysis, and more particularly to fabrication of microstructures in novel separation support media using laser ablation techniques. The microstructures produced under the present invention find use in any analysis system which is performed on either small and/or macromolecular solutes in the liquid phase and which may employ chromatographic or electrophoretic means of separation, or a combination of both.

BACKGROUND OF THE INVENTION

In sample analysis instrumentation, and especially in separation systems such as liquid chromatography and capillary electrophoresis systems, smaller dimensions will generally result in improved performance characteristics and at the same time result in reduced production and analysis costs. In this regard, miniaturized separation systems provide more effective system design, result in lower overhead due to decreased instrumentation sizing and additionally enable increased speed of analysis, decreased sample and solvent consumption and the possibility of increased detection efficiency.

Accordingly, several approaches towards miniaturization for liquid phase analysis have developed in the art; the conventional approach using drawn fused-silica capillary, and an evolving approach using silicon micromachining. What is currently thought of as conventional in miniaturization technology is generally any step toward reduction in size of the analysis system.

In conventional miniaturized technology the instrumentation has not been reduced in size; rather, it is the separation compartment size which has been significantly reduced. As an example, micro-column liquid chromatography ($\mu$LC) has been described wherein columns with diameters of 100–200 $\mu$m are employed as compared to prior column diameters of around 4.6 mm.

Another approach towards miniaturization has been the use of capillary electrophoresis (CE) which entails a separation technique carried out in capillaries 25–100 $\mu$m in diameter. CE has been demonstrated to be useful as a method for the separation of small solutes. *J. Chromatog.* 218:209 (1981); *Analytical Chemistry* 53:1298 (1981). In contrast, polyacrylamide gel electrophoresis was originally carried out in tubes 1 mm in diameter. Both of the above described "conventional" miniaturization technologies ($\mu$LC and CE) represent a first significant step toward reducing the size of the chemical portion of a liquid phase analytical system. However, even though experimentation with such conventional miniaturized devices has helped to verify the advantages of miniaturization in principle, there nevertheless remain several major problems inherent in those technologies.

For example, there remains substantial detection limitations in conventional capillary electrophoresis technology. For example, in CE, optical detection is generally performed on-column by a single-pass detection technique wherein electromagnetic energy is passed through the sample, the light beam travelling normal to the capillary axis and crossing the capillary only a single time. Accordingly, in conventional CE systems, the detection path length is inherently limited by the diameter of the capillary.

Given Beer's law, which relates absorbance to the pathlength through the following relationship:

$$A = \epsilon * b * C$$

where:
A=the absorbance
$\epsilon$=the molar absorptivity, (l/m,cm)
b=pathlength (cm)
C=concentration (m/l)

it can be readily understood that the absorbance (A) of a sample in a 25 $\mu$m capillary would be a factor of 400×less than it would be in a conventional 1 cm pathlength cell as typically used in UV/Vis spectroscopy.

In light of this significant detection limitation, there have been a number of attempts employed in the prior art to extend detection pathlengths, and hence the sensitivity of the analysis in CE systems. In U.S. Pat. No. 5,061,361 to Gordon, there has been described an approach entailing micro-manipulation of the capillary flow-cell to form a bubble at the point of detection. In U.S. Pat. No. 5,141,548 to Chervet, the use of a Z-shaped configuration in the capillary, with detection performed across the extended portion of the Z has been described. Yet another approach has sought to increase the detection pathlength by detecting along the major axis of the capillary (axial-beam detection). Xi et al., *Analytical Chemistry* 62:1580 (1990).

In U.S. Pat. No. 5,273,633 to Wang, a further approach to increased detection pathlengths in CE has been described where a reflecting surface exterior of the capillary is provided, the subject system further including an incident window and an exit window downstream of the incident window. Under Wang, light entering the incident window passes through a section of the capillary by multiple internal reflections before passing through the exit window where it is detected, the subject multiple internal reflections yielding an effective increase in pathlength. While each of the aforementioned approaches has addressed the issue of extending the pathlength, each approach is limited in that it entails engineering the capillary after-the-fact or otherwise increasing the cost of the analysis.

A second major drawback in the current approach to miniaturization involves the chemical activity and chemical instability of silicon dioxide ($SiO_2$) substrates, such as silica, quartz or glass, which are commonly used in both CE and $\mu$LC systems. More particularly, silicon dioxide substrates are characterized as high energy surfaces, in that such materials interact irreversibly with a number of compounds and strongly adsorb many compounds, most notably bases. The use of silicon dioxide materials in separation systems is further restricted due to the chemical instability of those substrates, as the dissolution of $SiO_2$ materials increases in basic conditions (at pH's greater than 7.0) due to the general weakness of the Si—O—Si bond.

To avoid the problems arising from the inherent chemical activity of silicon dioxide materials, prior separation systems have attempted chemical modifications to the inner silica surface of capillary walls. In general, such post-formation modifications are difficult as they require the provision of an interfacial layer to bond a desired surface treatment to the capillary surface, using, for example, sylating agents to create Si—O—Si—C bonds. Although such modifications may decrease the irreversible adsorption of solute molecules by the capillary surfaces, these systems still suffer from the chemical instability of Si—O—Si bonds at pH's above 7.0. Accordingly, chemical instability in $SiO_2$ materials remains a major problem.

However, despite the recognized shortcomings with the chemistry of $SiO_2$ substrates, those materials are still used in separation systems due to their desirable optical properties. In this regard, potential substitute materials which exhibit superior chemical properties compared to silicon dioxide materials are generally limited in that they are also highly adsorbing in the UV region, where detection is important.

In order to avoid some of the substantial limitations present in conventional μLC and CE techniques, and in order to enable even greater reduction in separation system sizes, there has been a trend towards providing planarized systems having capillary separation microstructures. In this regard, production of miniaturized separation systems involving fabrication of microstructures in silicon by micromachining or microlithographic techniques has been described. See, e.g. Fan et al., *Anal. Chem.* 66(1):177–184 (1994); Manz et al., *Adv. in Chrom.* 33:1–66 (1993); Harrison et al., *Sens. Actuators*, B B10(2): 107–116 (1993); Manz et al., *Trends Anal. Chem.* 10(5): 144–149 (1991); and Manz et al., *Sensors and Actuators B (Chemical)* B1(1–6) :249–255 (1990).

The use of micromachining techniques to fabricate separation systems in silicon provides the practical benefit of enabling mass production of such systems. In this regard, a number of established techniques developed by the microelectronics industry involving micromachining of planar materials, such as silicon, exist and provide a useful and well accepted approach to miniaturization. Examples of the use of such micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.

Micromachining silicon substrates to form miniaturized separation systems generally involves a combination of film deposition, photolithography, etching and bonding techniques to fabricate a wide array of three dimensional structures. Silicon provides a useful substrate in this regard since it exhibits high strength and hardness characteristics and can be micromachined to provide structures having dimensions in the order of a few micrometers.

Although silicon micromachining has been useful in the fabrication of miniaturized systems on a single surface, there are significant disadvantages to the use of this approach in creating the analysis device portion of a miniaturized separation system.

Initially, silicon micromachining is not amenable to producing a high degree of alignment between two etched or machined pieces. This has a negative impact on the symmetry and shape of a separation channel formed by micromachining, which in turn may impact separation efficiency. Secondly, sealing of micromachined silicon surfaces is generally carried out using adhesives which may be prone to attack by separation conditions imposed by liquid phase analyses. Furthermore, under oxidizing conditions, a silica surface is formed on the silicon chip substrate. In this regard, silicon micromachining is also fundamentally limited by the chemistry of $SiO_2$. Accordingly, there has remained a need for an improved miniaturized separation system which is able to avoid the inherent shortcomings of conventional miniaturization and silicon micromachining techniques.

SUMMARY OF THE INVENTION

The present invention relates to a miniaturized planar column device for use in a liquid phase analysis system. It is a primary object of the present invention to provide a miniaturized column device laser-ablated in a substantially planar substrate, wherein said substrate is comprised of a material selected to avoid the inherent chemical activity and pH instability encountered with silicon and prior silicon dioxide-based device substrates.

The present invention is also related to the provision of detection means engineered into a miniaturized planar column device whereby enhanced on-column analysis or detection of components in a liquid sample is enabled. It is further contemplated under the invention to provide a column device for liquid phase analysis having detection means designed into the device in significantly compact form as compared to conventional technology. In one particular aspect of the present invention, it is contemplated to provide optical detection means ablated in a miniaturized planar column device and having a substantially enhanced detection pathlength.

It is a further related object of the present invention to provide a device featuring improved means for liquid handling, including sample injection, and to provide a miniaturized column device with means to interface with a variety of external liquid reservoirs. Specifically contemplated herein is a system design which allows a variety of injection methods to be readily adapted to the planar structure, such as pressure injection, hydrodynamic injection or electrokinetic injection.

It is yet a further related object of the present invention to provide a miniaturized total chemical analysis system (μ-TAS) fully contained on a single, planar surface. In this regard, a miniaturized system according to the present invention is capable of performing complex sample handling, separation, and detection methods with reduced technician manipulation or interaction. Accordingly, the subject invention finds potential application in monitoring and/or analysis of components in industrial chemical, biological, biochemical and medical processes and the like.

A particular advantage of the present invention is the use of processes other than silicon micromachining techniques or etching techniques to create miniaturized columns in a wide variety of polymeric and ceramic substrates having desirable attributes for an analysis portion of a separation system. More specifically, it is contemplated herein to provide a miniaturized planar column device by ablating component microstructures in a substrate using laser radiation. In one preferred embodiment, a miniaturized column device is formed by providing two substantially planar halves having microstructures laser-ablated thereon, which, when the two halves are folded upon each other, define a separation compartment featuring enhanced symmetry and axial alignment.

Use of laser ablation techniques to form miniaturized devices according to the present invention affords several advantages over prior etching and micromachining techniques used to form systems in silicon or silicon dioxide materials. Initially, the capability of applying rigid computerized control over laser ablation processes allows microstructure formation to be executed with great precision, thereby enabling a heightened degree of alignment in structures formed by component parts. The laser ablation process also avoids problems encountered with microlithographic isotropic etching techniques which may undercut masking during etching, giving rise to asymmetrical structures having curved side walls and flat bottoms.

Laser ablation further enables the creation of microstructures with greatly reduced component size. In this regard, microstructures formed according to the invention are capable of having aspect ratios several orders of magnitude higher than possible using prior etching techniques, thereby providing enhanced separation capabilities in such devices. The use of laser-ablation processes to form microstructures in substrates such as polymers increases ease of fabrication and lowers per-unit manufacturing costs in the subject devices as compared to prior approaches such as micromachining devices in silicon. In this regard, devices formed under the invention in low-cost polymer substrates have the added feature of being capable of use as substantially disposable miniaturized column units.

In another aspect of the instant invention, laser-ablation in planar substrates allows for the formation of microstructures of almost any geometry or shape. This feature not only enables the formation of complex device configurations, but further allows for integration of sample preparation, sample injection, post-column reaction and detection means in a miniaturized total analysis system of greatly reduced overall dimensions.

The compactness of the analysis portion in a device produced under to the present invention, in conjunction with the feature that integral functions such as injection, sample handling and detection may be specifically engineered into the subject device to provide a µ-TAS device, further allows for integrated design of system hardware to achieve a greatly reduced system footprint.

By the present invention, inherent weaknesses existing in prior approaches to liquid phase separation device miniaturization, and problems in using silicon micromachining techniques to form miniaturized column devices have been addressed. Accordingly, the present invention discloses a miniaturized column device capable of performing a variety of liquid phase analyses on a wide array of liquid samples.

DETAILED DESCRIPTION OF THE PREFERRED EMBODIMENTS

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting.

In this specification and in the claims which follow, reference will be made to a number of terms which shall be defined to have the following meanings:

The term "substrate" is used herein to refer to any material which is UV-adsorbing, capable of being laser-ablated and which is not silicon or a silicon dioxide material such as quartz, fused silica or glass (borosilicates). Accordingly, it is contemplated under the present invention to form miniaturized column devices in suitable "substrates" such as laser ablatable polymers (including polyimides and the like) and in laser ablatable ceramics (including aluminum oxides and the like).

The term "liquid phase analysis" is used to refer to any analysis which is done on either small and/or macromolecular solutes in the liquid phase. Accordingly, "liquid phase analysis" as used herein includes chromatographic separations, electrophoretic separations, and electrochromatographic separations.

In this regard, "chromatographic" processes generally comprise preferential separations of components, and include reverse-phase, hydrophobic interaction, ion exchange, molecular sieve chromatography and like methods.

"Electrophoretic" separations refers to the migration of particles or macromolecules having a net electric charge where said migration is influenced by an electric field. Accordingly electrophoretic separations contemplated under the invention include separations performed in columns packed with gels (such as polyacrylamide, agarose and combinations thereof) as well as separations performed in solution.

"Electrochromatographic" separations refers to combinations of electrophoretic and chromatographic techniques.

The term "motive force" is used to refer to any means for inducing movement of a sample along a column in a liquid phase analysis, and includes application of an electric potential across any portion of the column, application of a pressure differential across any portion of the column or any combination thereof.

The term "surface treatment+ is used to refer to preparation or modification of the surface of a microchannel which will be in contact with a sample during separation, whereby the separation characteristics of the device are altered or otherwise enhanced. Accordingly, "surface treatment+ as used herein includes: physical surface adsorptions; covalent bonding of selected moieties to functional groups on the surface of microchannel substrates (such as to amine, hydroxyl or carboxylic acid groups on condensation polymers); methods of coating surfaces, including dynamic deactivation of channel surfaces (such as by adding surfactants to media), polymer grafting to the surface of channel substrates (such as polystyrene or divinyl-benzene) and thin-film deposition of materials such as diamond or sapphire to microchannel substrates.

The term "laser ablation" is used to refer to a machining process using a high-energy photon laser such as an excimer laser to ablate features in a suitable substrate. The excimer laser can be, for example, of the $F_2$, ArF, KrCl, KrF, or XeCl type.

In general, any substrate which is UV absorbing provides a suitable substrate in which one may laser ablate features. Accordingly, under the present invention, microstructures of selected configurations can be formed by imaging a lithographic mask onto a suitable substrate, such as a polymer or ceramic material, and then laser ablating the substrate with laser light in areas that are unprotected by the lithographic mask.

In laser ablation, short pulses of intense ultraviolet light are absorbed in a thin surface layer of material within about 1 μm or less of the surface. Preferred pulse energies are greater than about 100 millijoules per square centimeter and pulse durations are shorter than about 1 microsecond. Under these conditions, the intense ultraviolet light photo-dissociates the chemical bonds in the material. Furthermore, the absorbed ultraviolet energy is concentrated in such a small volume of material that it rapidly heats the dissociated fragments and ejects them away from the surface of the material. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micrometer.

Although laser ablation has been described herein using an excimer laser, it is to be understood that other ultraviolet light sources with substantially the same optical wavelength and energy density may be used to accomplish the ablation process. Preferably, the wavelength of such an ultraviolet light source will lie in the 150 nm to 400 nm range to allow high absorption in the substrate to be ablated. Furthermore, the energy density should be greater than about 100 millijoules per square centimeter with a pulse length shorter than about 1 microsecond to achieve rapid ejection of ablated material with essentially no heating of the surrounding remaining material. Laser ablation techniques, such as those described above, have been described in the art. Znotins, T. A., et al., *Laser Focus Electro Optics*, (1987) pp. 54–70; U.S. Pat. Nos. 5,291,226 and 5,305,015 to Schantz et al.

The term "injection molding" is used to refer to a process for molding plastic or nonplastic ceramic shapes by injecting a measured quantity of a molten plastic or ceramic substrate into dies (or molds). In one embodiment of the present invention, miniaturized column devices may be produced using injection molding.

More particularly, it is contemplated to form a mold or die of a miniaturized column device wherein excimer laser-ablation is used to define an original microstructure pattern in a suitable polymer substrate. The microstructure thus formed may then be coated by a very thin metal layer and electroplated (such as by galvano forming) with a metal such as nickel to provide a carrier. When the metal carrier is separated from the original polymer, an mold insert (or tooling) is provided having the negative structure of the polymer. Accordingly, multiple replicas of the ablated microstructure pattern may be made in suitable polymer or ceramic substrates using injection molding techniques well known in the art.

The term "LIGA process" is used to refer to a process for fabricating microstructures having high aspect ratios and increased structural precision using synchrotron radiation lithography, galvanoforming, and plastic molding. Under a LIGA process, radiation sensitive plastics are lithographically irradiated at high energy radiation using a synchrotron source to create desired microstructures (such as channels, ports, apertures and micro-alignment means), thereby forming a primary template.

The primary template is then filled with a metal by electrodeposition techniques. The metal structure thus formed comprises a mold insert for the fabrication of secondary plastic templates which take the place of the primary template. In this manner highly accurate replicas of the original microstructures may be formed in a variety of substrates using injection or reactive injection molding techniques. The LIGA process has been described by Becker, E. W., et al., *Microelectric Engineering* 4 (1986) pp. 35–56. Descriptions of numerous polymer substrates which may be injection molded using LIGA templates, and which are suitable substrates in the practice of the subject invention, may be found in "Contemporary Polymer Chemistry", Allcock H R and Lampe, F. W. (Prentice-Hall, Inc.) New Jersey (1981).

Accordingly, the invention concerns formation of miniaturized column devices using laser ablation in a suitable substrate. It is also contemplated to form column devices according to the invention using injection molding techniques wherein the original microstructure has been formed by an excimer laser ablation process, or where the original microstructure has been formed using a LIGA process.

More particularly, microstructures such as separation compartments, injection means, detection means and micro-alignment means may be formed in a planar substrate by excimer laser ablation. A frequency multiplied YAG laser may also be used in place of the excimer laser. In such a case, a complex microstructure pattern useful for practicing the invention may be formed on a suitable polymeric or ceramic substrate by combining a masking process with a laser ablation means, such as in a step-and-repeat process, where such processes would be readily understood by one of ordinary skill in the art.

In the practice of the invention, a preferred substrate comprises a polyimide material such as those available under the trademarks Kapton® or Upilex® from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof. Further, the polymer material selected may be produced in long strips on a reel, and, optional sprocket holes along the sides of the material may be provided to accurately and securely transport the substrate through a step-and-repeat process.

Under the invention, the selected polymer material is transported to a laser processing chamber and laser-ablated in a pattern defined by one or more masks using laser radiation. In a preferred embodiment, such masks define all of the ablated features for an extended area of the material, for example encompassing multiple apertures (including inlet and outlet ports), micro-alignment means and separation chambers.

Alternatively, patterns such as the aperture pattern, the separation channel pattern, etc., may be placed side by side on a common mask substrate which is substantially larger than the laser beam. Such patterns may then be moved sequentially into the beam. In other contemplated production methods, one or more masks may be used to form apertures through the substrate, and another mask and laser energy level (and/or number of laser shots) may be used to define separation channels which are only formed through a portion of the thickness of the substrate. The masking material used in such masks will preferably be highly reflecting at the laser wavelength, consisting of, for example, a multilayer dielectric material or a metal such as aluminum.

The laser ablation system employed in the invention generally includes beam delivery optics, alignment optics, a high precision and high speed mask shuttle system, and a processing chamber including mechanism for handling and positioning the material. In a preferred embodiment, the laser system uses a projection mask configuration wherein a precision lens interposed between the mask and the substrate projects the excimer laser light onto the substrate in the image of the pattern defined on the mask.

It will be readily apparent to one of ordinary skill in the art that laser ablation may be used to form miniaturized separation channels and apertures in a wide variety of geometries. Any geometry which does not include undercutting may be provided using ablation techniques, such as modulation of laser light intensity across the substrate, stepping the beam across the surface or stepping the fluence and number of pulses applied to each location to control corresponding depth. Further, laser-ablated channels or chambers produced according to the invention are easily fabricated having ratios of channel depth to channel width which are much greater than previously possible using etching techniques such as silicon micromachining. Such aspect ratios can easily exceed unity, and may even reach to 10.

In a preferred embodiment of the invention, channels of a semi-circular cross section are laser ablated by controlling exposure intensity or by making multiple exposures with the beam being reoriented between each exposure. Accordingly, when a corresponding semi-circular channel is aligned with a channel thus formed, a separation chamber of highly symmetrical circular cross-section is defined which may be desirable for enhanced fluid flow through the separation device.

As a final step in laser ablation processes contemplated by the invention, a cleaning step is performed wherein the laser-ablated portion of the substrate is positioned under a cleaning station. At the cleaning station, debris from the laser ablation are removed according to standard industry practice.

Figure 1:
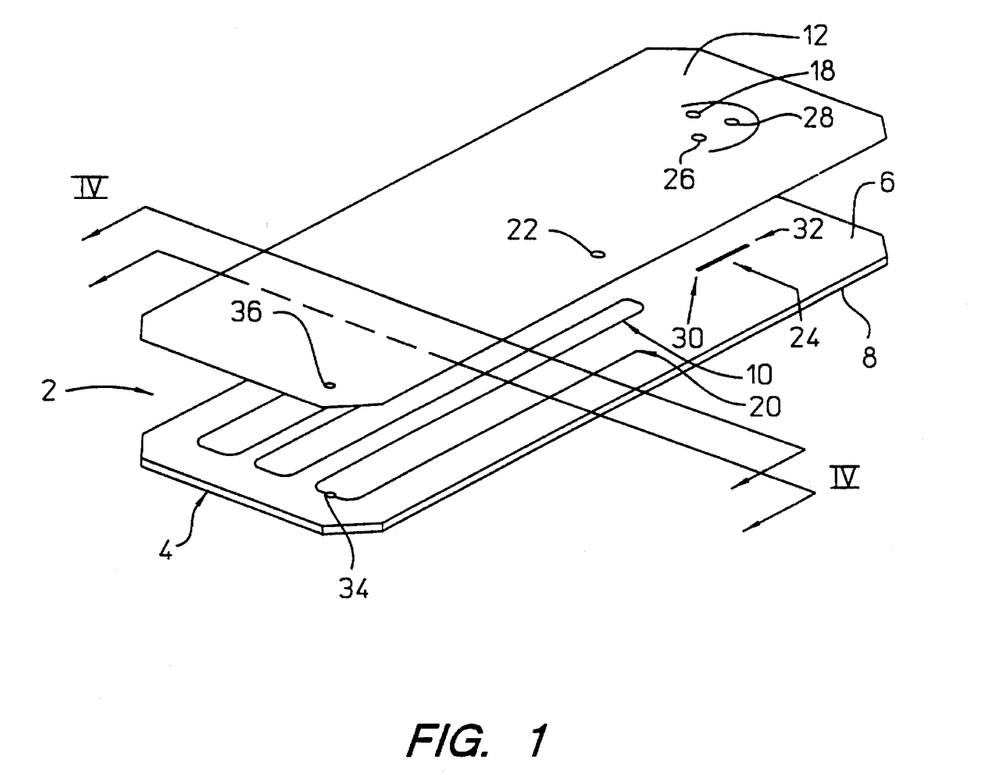
FIG. 1 is an exploded view of a miniaturized column device constructed in accordance with the present invention.

As will be appreciated by those working in the field of liquid phase analysis devices, the above-described method may be used to produce a wide variety of miniaturized devices. One such device is represented in FIG. 1 where a particular embodiment of a miniaturized column device is generally indicated at 2. Generally, miniaturized column 2 is formed in a selected substrate 4 using laser ablation techniques. The substrate 4 generally comprises first and second substantially planar opposing surfaces indicated at 6 and 8 respectively, and is selected from a material other than silicon which is UV absorbing and, accordingly, laser-ablatable.

In a particular embodiment of the invention, the miniaturized column device 2 comprises a column structure ablated on a chip, which, in the practice of the invention may be a machinable form of the plastic polyimide such as Vespel®. It is particularly contemplated in the invention to use such a polyimide substrate as, based on considerable experience with the shortcomings of fused silica and research into alternatives thereof, polyimides have proved to be a highly desirable substrate material for the analysis portion of a liquid phase separation system.

In this regard, it has been demonstrated that polyimides exhibit low sorptive properties towards proteins, which are known to be particularly difficult to analyze in prior silicon dioxide-based separation systems. Successful demonstrations of separations with this difficult class of solutes typically ensures that separation of other classes of solutes will be not be problematic. Further, since polyimide is a condensation polymer, it is possible to chemically bond groups to the surface which may provide a variety of desirable surface properties, depending on the target analysis. Unlike prior silicon dioxide based systems, these bonds to the polymeric substrate demonstrate pH stability in the basic region (pH 9–10).

Figure 2:
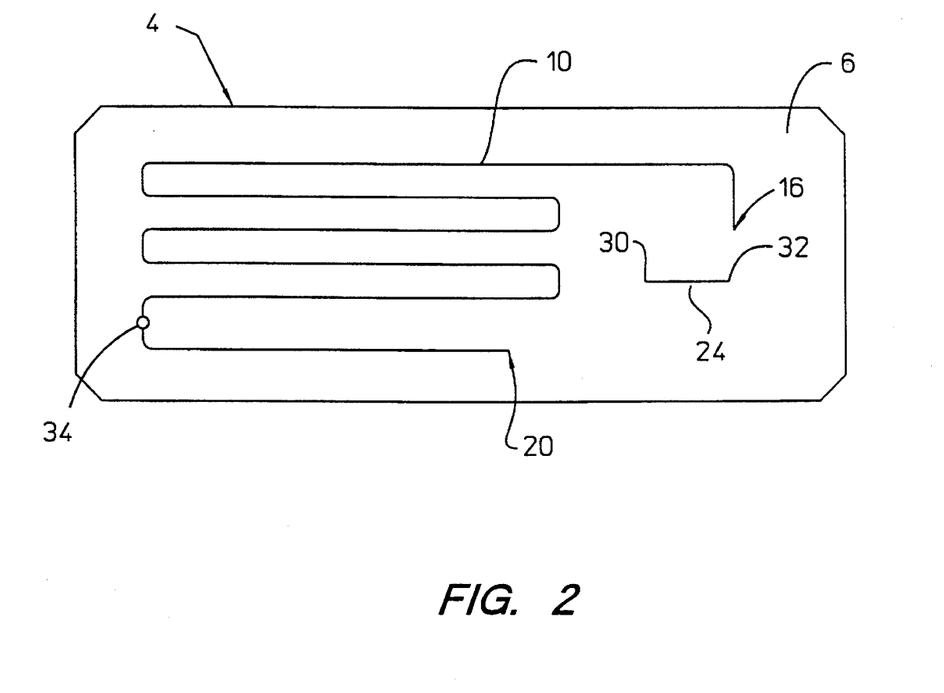
FIG. 2 is a plan view of the interior surface of the miniaturized column device of FIG. 1.
Figure 3:
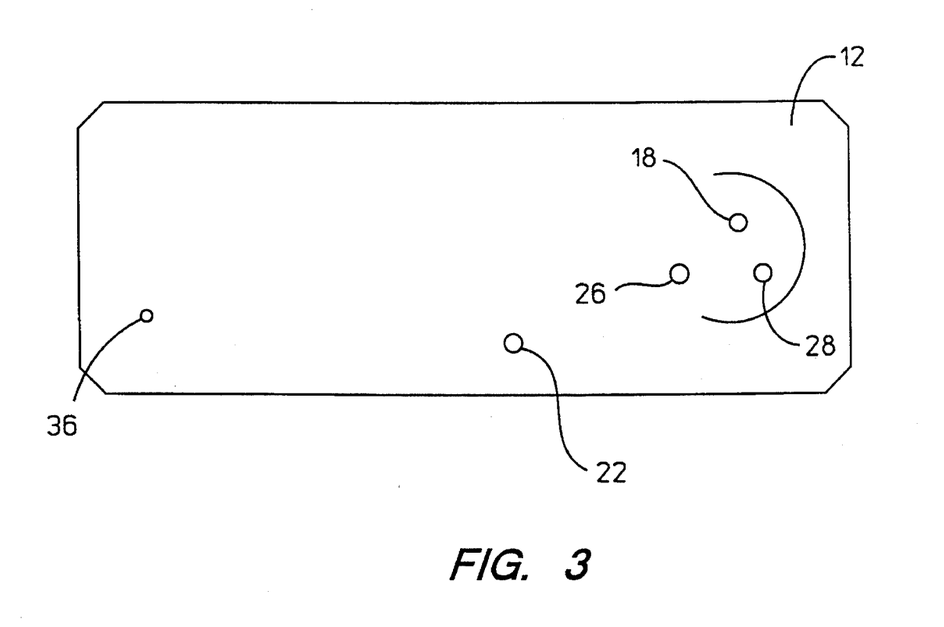
FIG. 3 is a plan view of the exterior surface of the device of FIG. 1.

Referring now to FIGS. 1–3, the substrate 4 has a microchannel 10 laser-ablated in a first planar surface 6. It will be readily appreciated that, although the microchannel 10 has been represented in a generally extended form, microchannels formed under the invention may be ablated in a large variety of configurations, such as in a straight, serpentine, spiral, or any tortuous path desired. Further, as described in greater detail above, the microchannel 10 may be formed in a wide variety of channel geometries including semi-circular, rectangular, rhomboid, and the like, and the channels may be formed in a wide range of aspect ratios. It is also noted that a device having a plurality of microchannels laser-ablated thereon falls within the spirit of the present invention.

Figure 4:
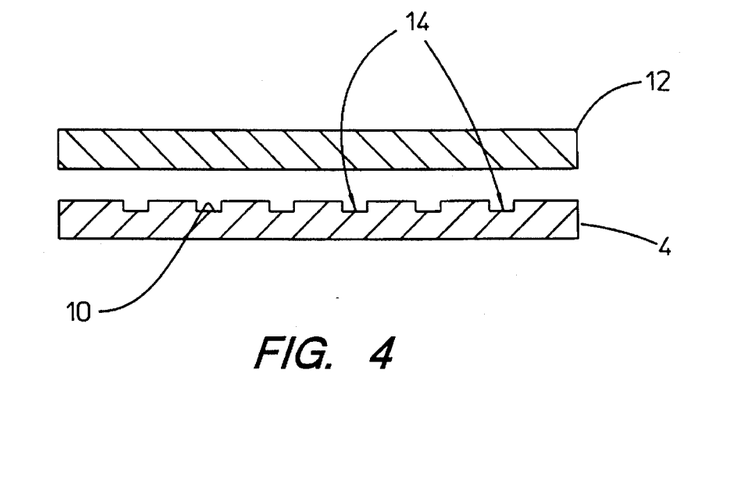
FIG. 4 is a cross-sectional side view of the miniaturized column device of FIG. 1, taken along lines IV—IV and showing formation of a separation compartment according to the invention.

Referring particularly to FIGS. 1 and 4, a cover plate 12 is arranged over said first planar surface 6 and, in combination with the laser-ablated microchannel 10, forms an elongate separation compartment 14. Cover plate 12 may be formed from any suitable substrate such as polyimide, the selection of the substrate only being limited by avoidance of undesirable separation surfaces such as silicon or silicon dioxide materials.

Under the invention, cover plate 12 may be fixably aligned over the first planar surface 6 to form a liquid-tight separation compartment by using pressure sealing techniques, by using external means to urge the pieces together (such as clips, tension springs or associated clamping apparatus) or by using adhesives well known in the art of bonding polymers, ceramics and the like.

Referring to FIGS. 1–3, a particular embodiment of the invention is shown wherein cover plate 12 further comprises apertures ablated therein. In this regard, a first aperture communicates with the separation compartment 14 at a first end 16 thereof to form an inlet port 18 enabling the passage of fluid from an external source into said separation compartment. A second aperture communicates with the separation compartment 14 at a second end 20 thereof to form an outlet port 22 enabling passage of fluid from the separation compartment to an external receptacle. Accordingly, a miniaturized column device is formed having a flow path extending from the first end 16 of the separation compartment and passing to the second end 20 thereof, whereby liquid phase analysis of samples may be carried out using techniques well known in the art.

Referring still to FIGS. 1–3, a particular embodiment of the invention is shown comprising sample introduction means laser-ablated into both the substrate 4 and cover plate 12. An internally ablated by-pass channel 24 is formed in substrate 4, said channel 24 being disposed near the first end 16 of the separation compartment. Two additional apertures 26 and 28 are formed in cover plate 12 and are arranged to cooperate with first and second ends (indicated at 30 and 32 respectively) of the by-pass channel 24. In this manner, a sample being held in an external reservoir may be introduced into by-pass channel 24 to form a sample plug of a known volume (defined by the dimensions of the channel 24). The sample plug thus formed may then be introduced into the first end 16 of the separation compartment 14 via inlet port 18 by communicating external mechanical valving with said inlet port and laser-ablated apertures 26 and 28 and flushing solution through the by-pass channel 24 into the separation compartment.

It is noted that the ablated by-pass channel 24 and apertures 26 and 28 further enable a wide variety of sample introduction techniques to be practiced under the invention. Particularly, having a by-pass channel which is not connected to the separation compartment allows a user to flush a sample through the by-pass channel without experiencing sample carry-over or column contamination. As will be appreciated by one of ordinary skill in the art after reading this specification, one such sample introduction technique may be effected by butt-coupling an associated rotor to a stator (not shown) on the external surface of a miniaturized column where the rotor selectively interfaces external tubing and fluid sources with inlet port 18 and apertures 26 and 28, allowing a sample to be flushed from the by-pass channel 24 into external tubing from which the sample may then be introduced into the column via inlet port 18 for liquid phase analysis thereof. In this regard, a miniaturized column device formed in a polyimide substrate enables a ceramic rotor, pressed to the device using tensioned force (to form a liquid-tight seal), to still rotate between selected aperture positions on the device due to the friction characteristics of the two materials.

Accordingly, in the practice of the invention, external hardware provides the mechanical valving necessary for communication of a miniaturized column device to different external liquid reservoirs, such as an electrolyte solution, flush solution or the sample via laser-ablated holes designed into the cover plate 12. This feature allows a variety of injection methods to be adapted to a miniaturized planar column device constructed according to the invention, including pressure injection, hydrodynamic injection or electrokinetic injection. In the particular embodiment of FIGS. 1–3, it is contemplated that external valving and injection means communicate with the separation device by butt-coupling to the laser-ablated apertures, however, any other suitable methods of connection known in the art may easily be adapted to the invention. Further, it is noted that numerous other sample introduction and fluid interfacing designs may be practiced and still fall within the spirit of the subject invention.

Also under the invention, a wide variety of means for applying a motive force along the length of the separation compartment 14 may be associated with the subject device. In this regard, a pressure differential or electric potential may be applied along the entire length of the separation compartment by interfacing motive means with inlet port 18 and outlet port 22

The use of substrates such as polyimides in the construction of miniaturized columns under the invention allows the possibility of using refractive-index (RI) detection to detect separated analytes of interest passing through the subject columns. In this regard, the provision of an associated laser diode which emits radiation at a wavelength where polyimide is "transparent" (such as at>450 nm) allows for a detection setup where no additional features need to be ablated in the column devices.

Referring now to FIGS. 2 and 3, in a preferred embodiment of the invention, detection means may be ablated into the substrate 4 and cover plate 12, where said detection means is disposed substantially downstream of the first end 16 of the separation compartment 14. More particularly, an aperture 34 may be ablated through substrate 4 to communicate with the separation compartment 14. A corresponding aperture 36 may be likewise formed in cover plate 12, and arranged so that it will be in co-axial alignment with aperture 34 when the cover plate is affixed to the substrate to form the separation compartment 14. In this manner, electrodes (not shown) may be connected to the miniaturized column device via the apertures 34 and 36 to detect separated analytes of interest passing through the separation compartment by electrochemical detection techniques.

Figure 5:
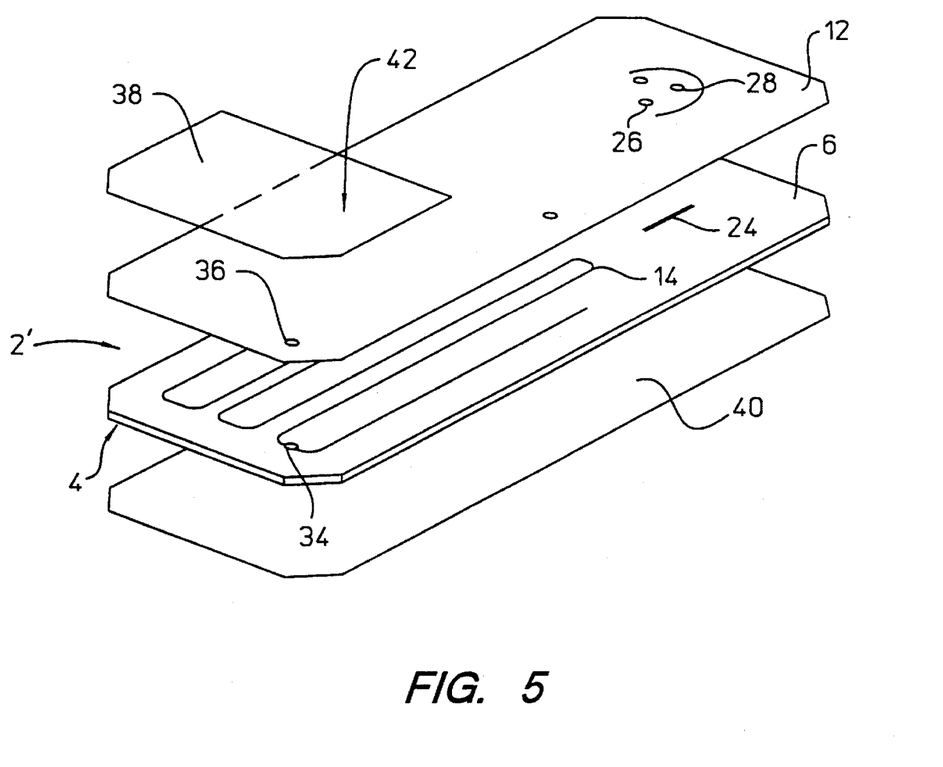
FIG. 5 is an exploded view of a preferred embodiment of the present invention including optical detection means.

Referring to FIG. 5, a further contemplated embodiment of the invention, indicated at 2' is shown comprising a preferred detection means indicated generally at 42. More particularly, a first transparent sheet 38 is provided wherein the cover plate 12 is interposed between said first transparent sheet and substrate 4. A second transparent sheet 40 is also provided wherein the second sheet is disposed over the second planar surface 8 of the substrate 4. In this manner, detection means 42 allows optical detection of separated analytes passing through separation compartment 14 via transmission of radiation orthogonal to the major axis of the separation compartment (and, accordingly, orthogonal to the direction of electro-osmotic flow in an electrophoretic separation). Further, in the practice of the invention, the transparent sheets may comprise materials such as quartz, diamond, sapphire, fused silica or any other suitable substrate which enables light transmission therethrough.

The subject transparent sheets may be formed with just enough surface area to cover and seal the detection apertures 34 and 36, or said sheets may be sized to cover up to the entire surface area of the column device. In this regard, additional structural rigidity may be provided to a column device formed in a particularly thin substrate film, such as a thin-film polyimide substrate, by employing a substantially coplanar sheet of, for example, fused silica.

Accordingly, the above described optical detection means 42 enables adaptation of a variety of external optical detection means to miniaturized columns constructed according to the invention. Further, sealing of the transparent sheets 38 and 40 to the miniaturized column device 2' is readily enabled, for example, when substrate 4 and cover plate 12 are formed in polyimide materials which include a layer of a thermal adhesive form of polyimide, since it is known that quartz/Kapton® bonds formed using such adhesives are very resilient. Sealing of other preferred transparent sheet materials, such as diamond, sapphire or fused-silica to the subject device may be accomplished using adhesion techniques well known in the art.

The possibility of detecting with radiation over a range of electromagnetic wavelengths offers a variety of spectrophotometric detection techniques to be interfaced with a miniaturized column according to the invention, including UV/Vis, fluorescence, refractive index (RI) and Raman.

Furthermore, as will be readily appreciated, the use of optical detection means comprising apertures ablated into the substrate and cover plate provides great control over the effective detection pathlength in a miniaturized column device constructed under the invention. In this regard, the detection pathlength will be substantially equal to the combined thickness of the substrate 4 and the cover plate 12, and detection pathlengths of up to 250 μm are readily obtainable using the subject detection means 42 in thin-film substrates such as polyimides.

Figure 6:
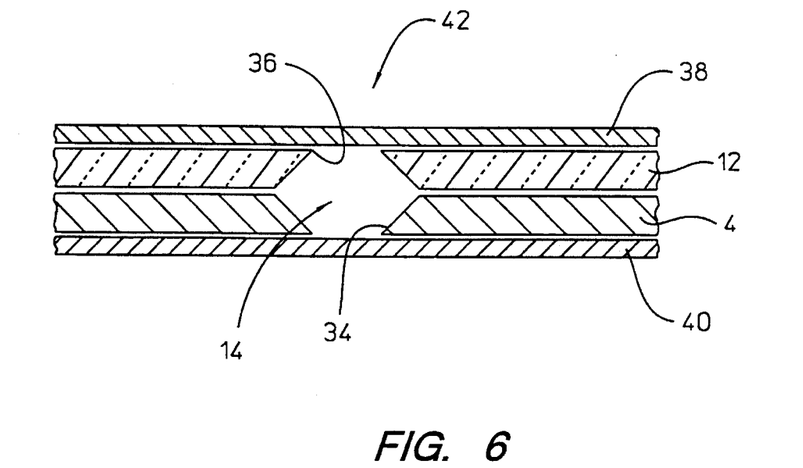
FIG. 6 is a cross-sectional axial view of the intersection of the separation compartment and the optical detection means in the miniaturized column device of FIG. 5.

Referring now to FIG. 6, it can be seen that apertures 34 and 36 provide an enlarged volume in separation compartment 14 at the point of intersection with the detection means 42, where that volume will be proportional to the combined thickness of substrate 4 and cover plate 12. In this manner, sample plugs passing through separation compartment 14 may be subject to untoward distortion as the plug is influenced by the increased compartment volume in the detection area, especially where the combined thickness of the substrate and cover plate exceeds about 250 μm, thereby possibly reducing separation efficiency in the device.

Accordingly, in the present invention wherein detection pathlengths exceeding 250 μm are desired, an alternative device embodiment may be provided having laser-ablated features on two opposing surfaces of a substrate. More particularly, in FIGS. 7 and 8, a further embodiment of a miniaturized column device constructed under the invention is generally indicated at 52. The miniaturized column comprises a substrate 54 having first and second substantially planar opposing surfaces respectively indicated at 56 and 58. The substrate 54 has a first microchannel 60 laser ablated in the first planar surface 56 and a second microchannel 62 laser ablated in the second planar surface 58, wherein said microchannels may be provided in a wide variety of geometries, configurations and aspect ratios as described in greater detail above.

Figure 7:
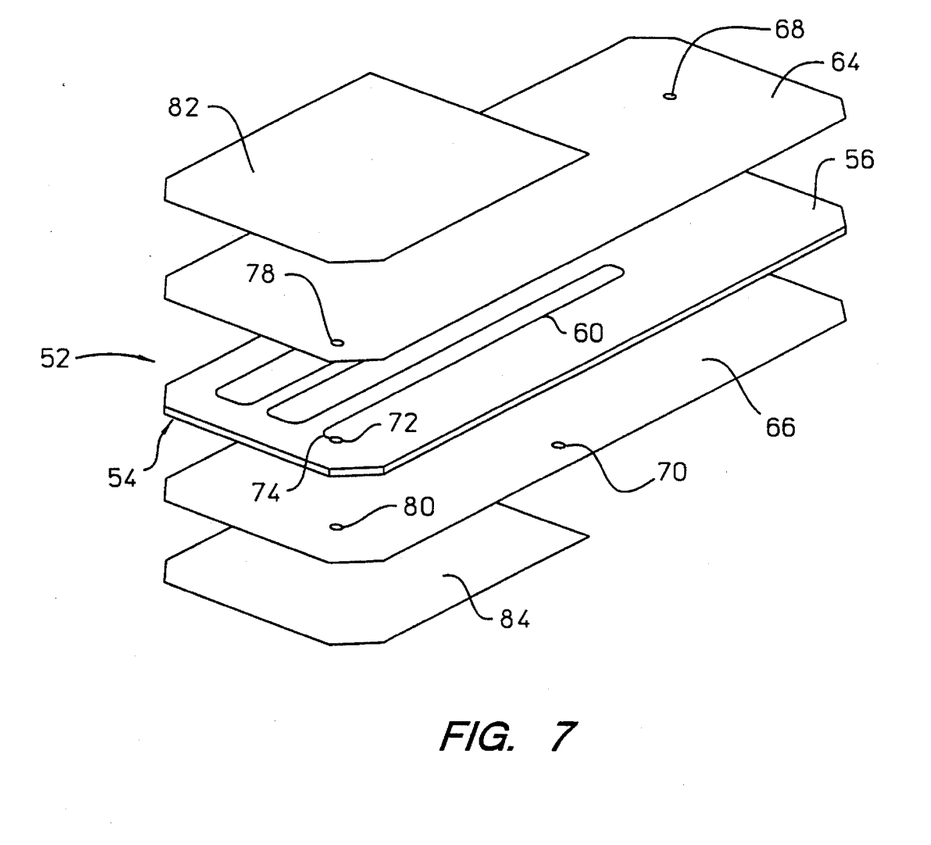
FIG. 7 is an exploded view of a first side of a miniaturized column device having microchannels formed on two opposing planar surfaces of a support substrate.
Figure 8:
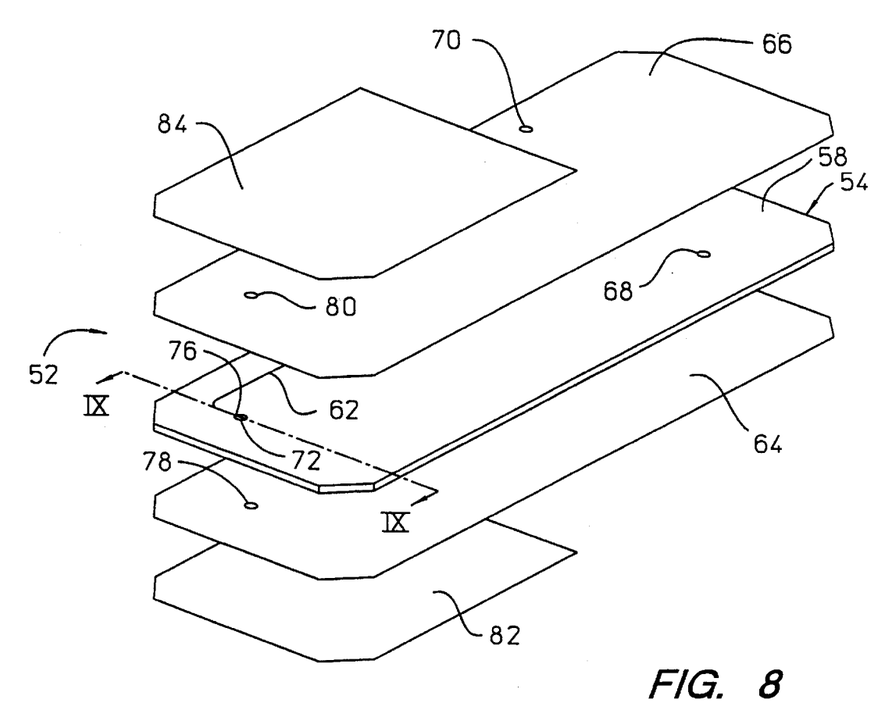
FIG. 8 is an exploded view of a second side of the column device of FIG. 7.

The miniaturized column device of FIGS. 7 and 8 further comprises first and second cover plates, indicated at 64 and 66 respectively, which, in combination with the first and second microchannels 60 and 62, define first and second elongate separation compartments when substrate 54 is sandwiched between said first and second cover plates.

Referring still to FIGS. 7 and 8, a plurality of apertures may be laser-ablated in the device to provide an extended separation compartment, and further to establish fluid communication means. More particularly, a conduit means 72, comprising a laser ablated aperture in substrate 54 having an axis which is orthogonal to said first and second planar surfaces 56 and 58, communicates a distal end 74 of said first microchannel 60 with a first end 76 of said second microchannel 62 to form an extended separation compartment.

Further, an aperture 68, laser ablated in the first cover plate 64, enables fluid communication with the first microchannel 60, and a second aperture 70, laser ablated in the second cover plate 66, enables fluid communication with the second microchannel 62. As will be readily appreciated, when said aperture 68 is used as an inlet port, and said second aperture 70 is used as an outlet port, a miniaturized column device is provided having a flow path extending along the combined length of said first and second microchannels 60 and 62.

In the embodiment of the invention as shown in FIGS. 7 and 8, a wide variety of sample introduction means may be employed, such as those described in detail above. External hardware may also be interfaced to the subject device to provide liquid handling capabilities, and a variety of means for applying a motive force along the length of the separation compartment may be associated with the device, such as by interfacing motive means with the first and/or second apertures 68 and 70 as described in greater detail above.

Additionally, detection means may easily be included in the subject embodiment. In this regard, a first aperture 78 may be laser ablated in the first cover plate 64, and a second aperture 80 may likewise be formed in the second cover plate 66 such that said first and second apertures will be in co-axial alignment with conduit means 72 when substrate 54 is sandwiched between said first and second cover plates. Accordingly, detection of analytes in a separated sample passing through the conduit means is easily enabled, such as by connecting electrodes to the miniaturized column via apertures 78 and 80 and detecting using electrochemical techniques.

Figure 9:
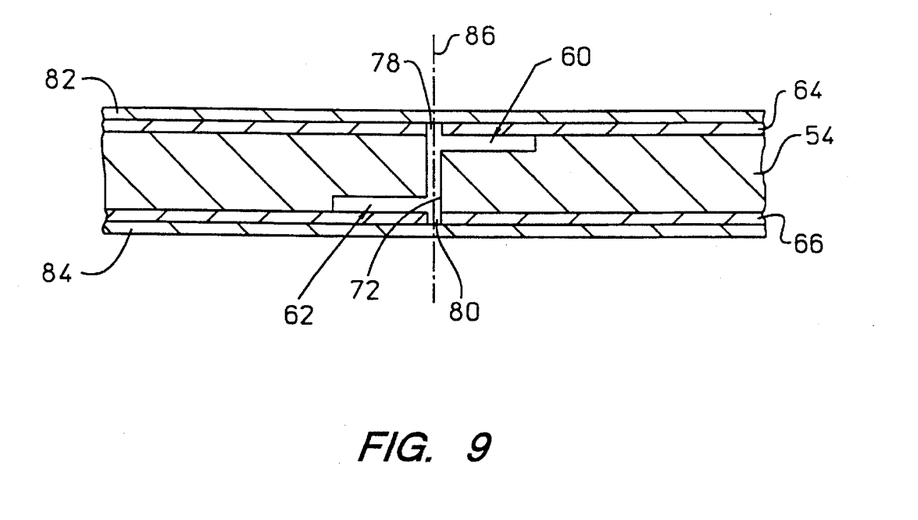
FIG. 9 is a cross-sectional trans-axial view of the extended optical detection pathlength in the miniaturized column of FIG. 8 taken along lines IX—IX.

However, a key feature of the laser-ablated conduit means 72 in the invention is the ability to provide an extended optical detection pathlength of up to 1 mm, or greater, without experiencing untoward sample plug distortion due to increased separation compartment volumes at the point of detection. Referring to FIGS. 7–9, first and second transparent sheets, indicated at 82 and 84 respectively, may be provided such that the first cover plate 64 is interposed between said first transparent sheet and the first planar surface 56, and the second cover plate 66 is interposed between said second transparent sheet and the second planar surface 58. Under the invention, transparent sheets 82 and 84 may be selected from materials such as quartz crystal, fused silica, diamond, sapphire and the like. Further, said transparent sheets may be provided having just enough surface area to cover and seal the apertures 78 and 80, or said sheets may be sized to cover up to the entire surface area of the column device. As described in greater detail above, this feature allows additional structural rigidity to be provided to a column device formed in a particularly thin substrate.

As best shown in FIG. 9, the subject arrangement allows optical detection of sample analytes passing through the miniaturized column device to be carried out along an optical detection pathlength 86 corresponding to the major axis of the conduit means 72. As will be readily appreciated, the optical detection pathlength 86 is substantially determined by the thickness of the substrate 54, and, accordingly, a great deal of flexibility in tailoring a miniaturized column device having μ-meter column dimensions and optical pathlengths of up to 1 mm or greater is thereby enabled under the instant invention. In this manner, a wide variety of associated optical detection devices may be interfaced with a miniaturized column constructed under the invention, and detection of analytes in samples passing through the conduit means 72 may be carried out using UV/Vis, fluorescence, refractive index (RI), Raman and like spectrophotometric techniques.

Accordingly, novel miniaturized column devices have been described which are laser ablated into a substrate other than silicon or silicon dioxide materials, and which avoid several major problems which have come to be associated with prior attempts at providing micro-column devices. The use of laser ablation techniques in the practice of the invention enables highly symmetrical and accurately defined micro-column devices to be fabricated in a wide class of polymeric and ceramic substrates to provide a variety of miniaturized liquid-phase analysis systems. In this regard, miniaturized columns may be provided which have microcapillary dimensions (ranging from 20–200 μm in diameter) and column detection pathlengths of up to 1 mm or greater. This feature has not been attainable in prior attempts at miniaturization, such as in capillary electrophoresis, without substantial engineering of a device after capillary formation. Further, laser ablation of miniaturized columns in inert substrates such as polyimides avoids the problems encountered in prior devices formed in silicon or silicon dioxide-based materials. Such problems include the inherent chemical activity and pH instability of silicon and silicon dioxide-based substrates which limits the types of separations capable of being performed in those devices.

In the practice of the invention, miniaturized column devices may be formed by laser ablating a set of desired features in a selected substrate using a step-and-repeat process to form discrete units. In this regard, it is particularly contemplated to laser ablate the subject devices in condensation polymer substrates including polyimides, polyamides, poly-esters and polycarbonates. Further, the instant invention may be practiced using either a laser ablation process or a LIGA process to form templates encompassing a set of desired features, whereby multiple copies of miniaturized columns may be mass-produced using injection molding techniques well known in the art. More particularly, it is contemplated herein to form miniaturized columns by injection molding in substrates comprised of materials such as the following: polycarbonates; polyesters, including poly(ethylene terephthalate) and poly(butylene terephthalate); polyamides, (such as nylons); polyethers, including polyformaldehyde and poly(phenylene sulfide); polyimides, such as Kapton® and Upilex®; polyolefin compounds, including ABS polymers, Kel-F copolymers, poly(methyl methacrylate), poly(styrene-butadiene) copolymers, poly(tetrafluoroethylene), poly(ethylenevinyl acetate) copolymers, poly(N-vinylcarbazole) and polystyrene.

Laser ablation of microchannels in the surfaces of the above-described substrates has the added feature of enabling a wide variety of surface treatments to be applied to the microchannels before formation of the separation compartment. That is, the open configuration of laser-ablated microchannels produced using the method of the invention enables a number of surface treatments or modifications to be performed which are not possible in closed format constructions, such as in prior microcapillaries. More specifically, laser ablation in condensation polymer substrates provides microchannels with surfaces featuring functional groups, such as carboxyl groups, hydroxyl groups and amine groups, thereby enabling chemical bonding of selected species to the surface of the subject microchannels using techniques well known in the art. Other surface treatments enabled by the open configuration of the instant devices include surface adsorptions, polymer graftings and thin film deposition of materials such as diamond or sapphire to microchannel surfaces using masking and deposition techniques and dynamic deactivation techniques well known in the art of liquid separations.

The ability to exert rigid computerized control over the present laser ablation processes enables extremely precise microstructure formation, which, in turn, enables the formation of miniaturized columns having features ablated in two substantially planar components wherein those components may be aligned to define a composite separation compartment of enhanced symmetry and axial alignment. In this regard, it is contemplated to provide a further embodiment of the invention wherein laser ablation is used to create two component halves which, when folded or aligned with one another, define a single miniaturized column device.

Figure 10:
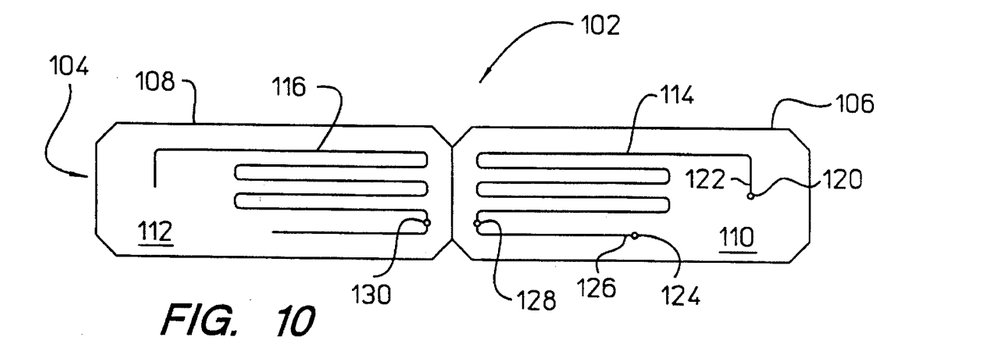
FIG. 10 is plan view of a miniaturized column device constructed under the invention having first and second component halves.

Referring now to FIG. 10, a miniaturized column for liquid phase analysis of a sample is generally indicated at 102. The miniaturized column 102 is formed by providing a support body 104 having first and second component halves indicated at 106 and 108 respectively. The support body may comprise a substantially planar substrate such as a polyimide film which is both laser ablatable and flexible so as to enable folding after ablation; however, the particular substrate selected is not considered to be limiting in the invention.

The first and second component halves 106 and 108 each have substantially planar interior surfaces, indicated at 110 and 112 respectively, wherein miniaturized column features may be laser ablated. More particularly, a first microchannel pattern 114 is laser ablated in the first planar interior surface 110 and a second microchannel pattern 116 is laser ablated in the second planar interior surface 112. Under the invention, said first and second microchannel patterns are ablated in the support body 104 so as to provide the mirror image of each other.

Figure 11:
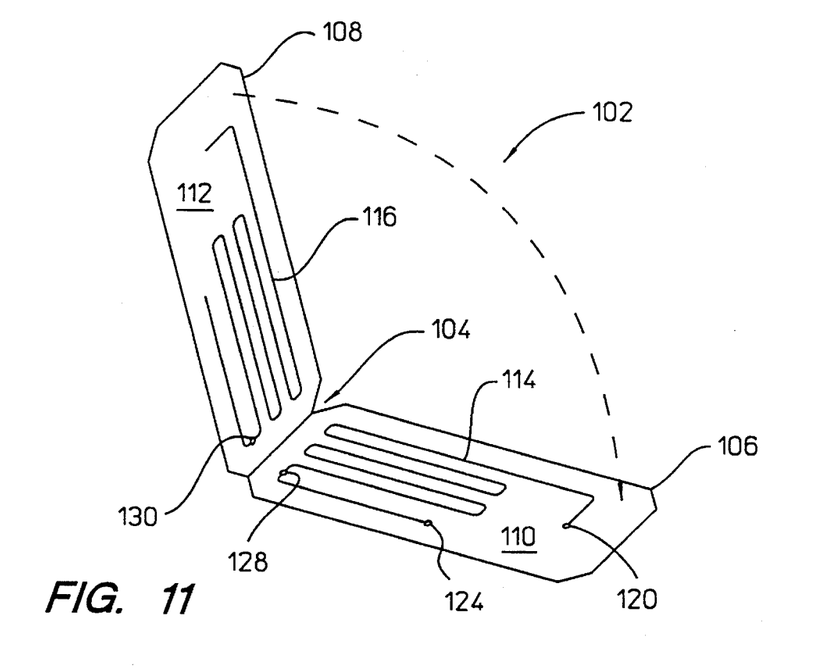
FIG. 11 is a pictorial representation of the column device of FIG. 10 showing the folding alignment of the component halves to form a single device.
Figure 12:
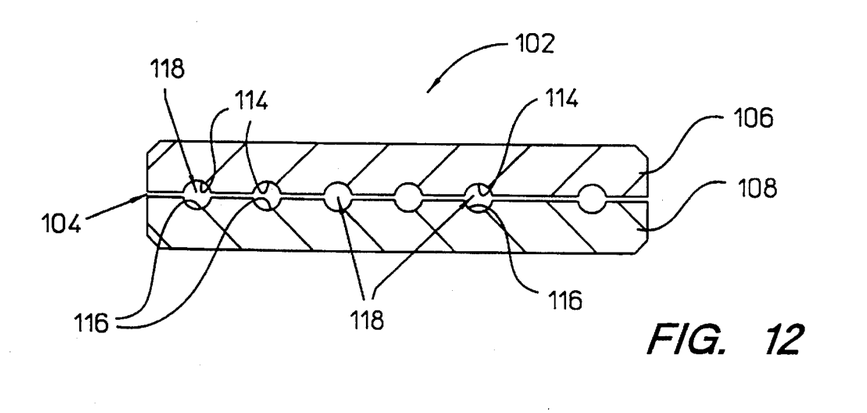
FIG. 12 is a cross-sectional axial view of the separation compartment formed by the alignment of the component halves in the device of FIG. 10.

Referring now to FIGS. 11 and 12, a separation compartment 118, comprising an elongate bore defined by the first and second microchannel patterns 114 and 116 may be formed by aligning (such as by folding) the first and second component halves 106 and 108 in facing abutment with each other. In the practice of the invention, the first and second component halves may be held in fixable alignment with one another to form a liquid-tight separation compartment using pressure sealing techniques, such as by application of tensioned force, or by use of adhesives well known in the art of liquid phase separation devices. It is further contemplated under the invention to form first and second microchannels 114 and 116 having semi-circular cross-sections whereby alignment of the component halves defines a separation compartment 118 having a highly symmetrical circular cross-section to enable enhanced fluid flow therethrough; however, as discussed above, a wide variety of microchannel geometries are also within the spirit of the invention.

In a further preferred embodiment of the invention, it is particularly contemplated to form the support body 104 from a polymer laminate substrate comprising a Kapton® film co-extruded with a thin layer of a thermal plastic form of polyimide referred to as KJ and available from DuPont (Wilmington, Del.). In this manner, the first and second component halves 106 and 108 may be heat sealed together, resulting in a liquid-tight weld that has the same chemical properties and, accordingly, the same mechanical, electrical and chemical stability, as the bulk Kapton® material.

Referring now to FIGS. 10–12, the miniaturized column device 102 further comprises means for communicating associated external fluid containment means (not shown) with the separation compartment 118 to provide a liquid-phase separation device. More particularly, a plurality of apertures may be laser ablated in the support body 104, wherein said apertures extend from at least one exterior surface of the support body and communicate with at least one microchannel, said apertures permitting the passage of fluid therethrough. In this regard, an inlet port 120 may be laser ablated in the first component half 106 and communicate with a first end 122 of said first microchannel 114. In the same manner, an outlet port 124 may be ablated in the first component half and communicate with a second end 126 of said first microchannel 114.

As is readily apparent, a liquid phase separation device may thereby be formed, having a flow path extending from the first end 122 of the microchannel 114 to the second end 126 thereof, by communicating fluids from an associated source (not shown) through the inlet port 120, passing the fluids through the separation compartment 118 formed by the alignment of microchannels 114 and 116, and allowing the fluids to exit the separation compartment via the outlet port 126. In this manner, a wide variety of liquid phase analysis procedures may be carried out in the subject miniaturized column device using techniques well known in the art. Furthermore, various means for applying a motive force along the length of the separation compartment 118, such as a pressure differential or electric potential, may be readily interfaced to the column device via the inlet and outlet ports, or by interfacing with the separation compartment via additional apertures which may be ablated in the support body 104.

Inlet port 120 may be formed such that a variety of external fluid and/or sample introduction means may be readily interfaced with the miniaturized column device 102. As discussed in greater detail above, such means include external pressure injection, hydrodynamic injection or electrokinetic injection mechanisms.

Referring now to FIGS. 10 and 11, the miniaturized column device 102 further comprises detection means laser ablated in the support body 104. More particularly, a first aperture 128 is ablated in said first component half 106 and communicates with the first microchannel 114 at a point near the second end 126 thereof. A second aperture 130 is likewise formed in said second component half 108 to communicate with the second microchannel 116. Accordingly, a wide variety of associated detection means may then be interfaced to the separation compartment 118 to detect separated analytes of interest passing therethrough, such as by connection of electrodes to the miniaturized column via the first and second apertures 128 and 130.

In yet a further preferred embodiment of the invention, an optical detection means is provided in the miniaturized column device 102. In this regard, first and second apertures 128 and 130 may be ablated in the support body 104 such that when the component halves are aligned to form the separation compartment 118 said apertures are in co-axial alignment with one another, said apertures further having axes orthogonal to the plane of said support body. As will be readily appreciated by one of ordinary skill in the art, by providing transparent sheets (not shown), disposed over the exterior of the support body 104 and covering said first and second apertures 128 and 130, a sample passing through separation compartment 118 may be analyzed by interfacing spectrophotometric detection means with said sample through the transparent sheets using techniques well known in the art. The optical detection pathlength may be substantially determined by the combined thickness of said first and second component halves 106 and 108. In this manner, an optical detection pathlength of up to 250 μm is readily provided by ablating the miniaturized column device in a 125 μm polymer film.

Accordingly, there have been described several preferred embodiments of a miniaturized column device formed according to the invention by laser ablating microstructures on component parts and aligning the components to form columns having enhanced symmetries. As described in detail above, formation of the subject microchannels in the open configuration enables a wide variety of surface treatments and modifications to be applied to the interior surfaces of the channels before formation of the separation compartment. In this manner, a wide variety of liquid phase analysis techniques may be carried out in the composite separation compartments thus formed, including chromatographic, electrophoretic and electrochromatographic separations.

In the practice of the invention, it is further contemplated to provide optional means for the precise alignment of component support body halves, thereby ensuring accurate definition of a composite separation compartment formed under the invention. More particularly, in a further preferred embodiment of the invention, micro-alignment means are provided to enable enhanced alignment of laser-ablated component parts such as microchannels, detection apertures and the like.

Figure 13:
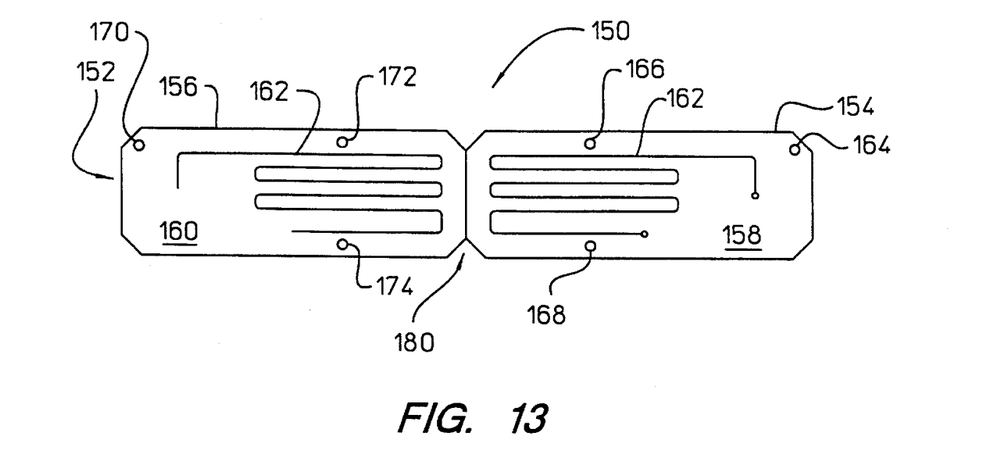
FIG. 13 is a plan view of a further preferred embodiment of the present invention having optional micro-alignment means on first and second component halves.
Figure 14:
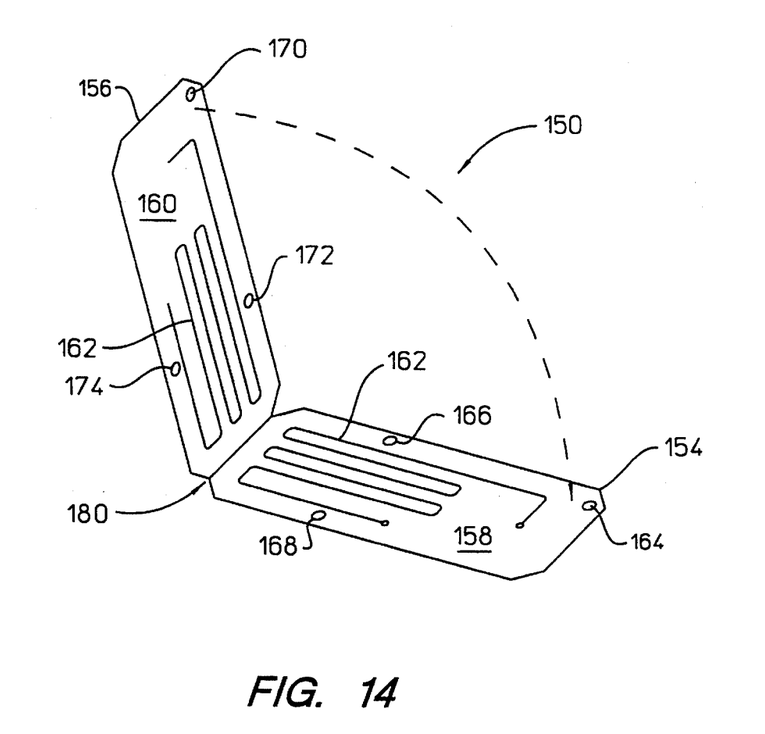
FIG. 14 is a pictorial representation of the column device of FIG. 13 showing the micro-alignment of the component halves.

Referring now to FIGS. 13 and 14, a miniaturized column device constructed according to the present invention is generally indicated at 150 and is formed in a flexible substrate 152. The column device comprises first and second support body halves, indicated at 154 and 156 respectively, each having a substantially planar interior surface indicated at 158 and 160 respectively. The interior surfaces comprise laser-ablated microstructures, generally indicated at 162, where said microstructures are arranged to provide the mirror image of one another in the same manner as described in greater detail above.

The accurate alignment of component parts may be enabled by forming a miniaturized column device in a flexible substrate 152 having at least one fold means, generally indicated at 180, such that a first body half 154 may be folded to overlie a second body half 156. The fold means 180 may comprise a row of spaced-apart perforations ablated in the substrate 152, spaced-apart slot-like depressions or apertures ablated so as to extend only part way through the substrate, or the like. The perforations or depressions may have circular, diamond, hexagonal or other shapes that promote hinge formation along a predetermined straight line.

Accordingly, in the practice of the invention, the fold means 180 allows said first and second support body halves 154 and 156 to hingably fold upon one another and accurately align composite features defined by said microstructures ablated on said first and second planar interior surfaces 158 and 160.

It is further contemplated to provide additional micro-alignment means formed either by laser ablation or by other methods of fabricating shaped pieces well known in the art. More specifically, a plurality of laser-ablated apertures (not shown) may be provided in said first and second support body halves 154 and 156 where said apertures are so arranged such that co-axial alignment thereof enables the precise alignment of the support body halves to define composite features such as an ablated elongate bore. Alignment may be effected using an external apparatus with means (such as pins) for cooperating with said co-axial apertures to maintain the body halves in proper alignment with one another.

Referring to FIGS. 13 and 14, in yet another particular embodiment of the invention, micro-alignment means may been formed in said first and second support body halves 154 and 156 using fabrication techniques well known in the art e.g., molding or the like. In this manner, a plurality of projections, indicated at 164, 166 and 168, may be formed in said first support body half 154. A plurality of depressions, indicated at 170, 172 and 174, may be formed in said second support body half 156.

Accordingly, as is readily apparent, the micro-alignment means are configured to form corresponding structures with one another, whereby projection 164 mates with depression 170, projection 166 mates with depression 172, and projection 168 mates with depression 174 when said support body halves are aligned in facing abutment with one another. In this manner, positive and precise alignment of support body halves 154 and 156 is enabled, thereby accurately defining composite features defined by said laser-ablated microstructures 162.

As will be readily apparent to one of ordinary skill in the art after reading this specification, a wide variety of corresponding micro-alignment features may be formed in the subject miniaturized column devices without departing from the spirit of the instant invention. Such additional features include any combination of holes and/or corresponding structures such as grooves and ridges in said component parts where said features cooperate to enable precise alignment of the component body parts.

Further, while the present invention has been described with reference to specific preferred embodiments, it is understood that the description and examples included herein are intended to illustrate and not limit the scope of the invention, which is defined by the scope of the appended claims.

We claim:

1. A method of forming a miniaturized column device comprising the steps of:
   (a) providing a support body having first and second component halves, said support body halves having substantially planar interior surfaces;
   (b) forming a compartment in said support body by: (i) laser ablating a first microchannel in the interior surface of said first support body half; (ii) laser ablating a second microchannel in the interior surface of said second support body half, said second microchannel so arranged as to provide the mirror image of said first microchannel; and (iii) aligning said interior surfaces of said support body halves in facing abutment with each other whereby said microchannels define an elongate bore;
   (c) forming a plurality of ports in said support body, said ports enabling fluid communication between said compartment and associated external fluid containment means, wherein said step of forming said ports comprises laser ablating a plurality of apertures extending from at least one exterior surface of said support body and communicating with at least one microchannel, said apertures permitting the passage of fluid therethrough; and
   (d) forming detection means in said support body by laser ablating apertures through said first and second component halves, said apertures communicating with said compartment.

2. The method of claim 1, including the additional step of forming fold means in the support body, wherein the step of forming said fold means comprises laser-ablating a row of spaced-apart perforations in the support body to define a hinge whereby the support body may be folded about said hinge with said first and second component halves placed in precise alignment with one another.

3. The method of claim 2, including the additional step of forming micro-alignment means in said first and second support body halves by laser-ablating holes in said support body halves, said holes so arranged whereby co-axial alignment of said holes enables the precise alignment of said support body halves to accurately define said elongate bore.

4. The method of claim 2, including the additional step of providing micro-alignment means in said support body halves by forming corresponding structures, said structures comprising a plurality of depressions arranged on a first support body half and a plurality of projections arranged on a second support body half wherein said projections are configured to mate with said depressions, said structures arranged on said support body halves whereby the mating thereof enables the precise alignment of said support body halves to accurately define said elongate bore.

5. The method of claim 1, including the additional step of subjecting said first and second microchannels to a surface treatment after said microchannels are laser ablated in the surface of said support body halves and before said separation compartment is formed, wherein the surface treatment comprises chemical bonding or adsorption of a selected species to the interior surface of the laser-ablated microchannels or thin film deposition of a selected material thereon.

6. The method of claim 1, including the additional steps of:

providing said support body as a laminate, said laminate formed from a first layer of polyimide co-extruded with a second, thin layer of a thermal adhesive form of polyimide; and heat sealing said first and second support body halves together using heat stacking whereby a weld is formed having substantially the same physical and chemical properties as said support body.

* * * * *